US012599574B2

(12) United States Patent
Chung et al.

(10) Patent No.: US 12,599,574 B2
(45) Date of Patent: Apr. 14, 2026

(54) PROCESS OF MAKING MEMBRANE LIPID COATED NANOPARTICLES

(71) Applicant: Coastar Therapeutics Inc., San Diego, CA (US)

(72) Inventors: Eddie Yocon Chung, La Jolla, CA (US); Han Liang Lim, San Diego, CA (US)

(73) Assignee: Coastar Therapeutics Inc., San Diego, CA (US)

( * ) Notice: Subject to any disclaimer, the term of this patent is extended or adjusted under 35 U.S.C. 154(b) by 981 days.

(21) Appl. No.: 17/627,643

(22) PCT Filed: Jul. 16, 2020

(86) PCT No.: PCT/US2020/042420
§ 371 (c)(1),
(2) Date: Jan. 15, 2022

(87) PCT Pub. No.: WO2021/011826
PCT Pub. Date: Jan. 21, 2021

(65) Prior Publication Data
US 2022/0354802 A1      Nov. 10, 2022

Related U.S. Application Data

(60) Provisional application No. 62/874,978, filed on Jul. 16, 2019.

(51) Int. Cl.
*A61K 9/51*      (2006.01)
*A61K 9/50*      (2006.01)
*A61K 35/761*      (2015.01)

*A61K 35/763*      (2015.01)
*A61K 35/768*      (2015.01)

(52) U.S. Cl.
CPC .......... *A61K 9/5192* (2013.01); *A61K 9/5068* (2013.01); *A61K 35/761* (2013.01); *A61K 35/763* (2013.01); *A61K 35/768* (2013.01)

(58) Field of Classification Search
None
See application file for complete search history.

(56)      References Cited

U.S. PATENT DOCUMENTS

2003/0220284 A1      11/2003      Yotnda et al.
2009/0041724 A1      2/2009      Jensen
(Continued)

FOREIGN PATENT DOCUMENTS

CN      109288875 A      2/2019
JP      2005535730 A      11/2005
(Continued)

OTHER PUBLICATIONS

Dumard et al. "Full inactivation of human influenza virus by high hydrostatic pressure preserves virus structure and membrane fusion while conferring protection to mice against infection" PLoS One (2013); 8(11):e80785, 13 pages.
(Continued)

*Primary Examiner* — Jeffrey D Washville
(74) *Attorney, Agent, or Firm* — Cooley LLP

(57)      ABSTRACT
Disclosed is a process of making a nanoparticle comprising an inner core comprising a virus and an outer surface comprising a cellular membrane derived from a cell via extrusion.

14 Claims, 2 Drawing Sheets

(56) References Cited

U.S. PATENT DOCUMENTS

| | | | |
|---|---|---|---|
| 2013/0323206 A1 | 12/2013 | Yun et al. | |
| 2013/0337066 A1* | 12/2013 | Zhang | A61K 9/148 |
| | | | 424/234.1 |
| 2014/0017298 A1 | 1/2014 | John et al. | |
| 2014/0271813 A1 | 9/2014 | Richter et al. | |
| 2015/0182460 A1 | 7/2015 | Hong et al. | |
| 2017/0252413 A1* | 9/2017 | Esener | A61K 9/5115 |
| 2021/0299244 A1* | 9/2021 | Mosharraf | A61K 47/6911 |
| 2024/0108716 A1* | 4/2024 | Steinmetz | A61K 39/215 |
| 2024/0325314 A1 | 10/2024 | Chung | |

FOREIGN PATENT DOCUMENTS

| | | |
|---|---|---|
| JP | 2020519241 A | 7/2020 |
| WO | WO-2009053937 A2 | 4/2009 |
| WO | WO-2018195526 A1 | 10/2018 |
| WO | WO-2021011826 A1 | 1/2021 |

OTHER PUBLICATIONS

Han, Sy et al. "Gene transfer using liposome-complexed adenovirus seems to overcome limitations due to coxsackievirus and adenovirus receptor-deficiency of cancer cells, both in vitro and in vivo" Experimental & Molecular Medicine (2008); 40(4):427-434.

Hu, Che-Ming J. et al. "Erythrocyte membrane-camouflaged polymeric nanoparticles as a biomimetic delivery platform" Proceedings of the National Academy of Sciences (2011); 108(27):10980-10985.

Hunter et al. "Effect of extrusion pressure and lipid properties on the size and polydispersity of lipid vesicles" Biophysical Journal (1998); 74(6):2996-3002.

Luk et al. "Interfacial interactions between natural RBC membranes and synthetic polymeric nanoparticles" Nanoscale (2014); 6(5):2730-2737.

Lv, P. et al. "Genetically engineered cell membrane nanovesicles for oncolytic adenovirus delivery: A versatile platform for cancer virotherapy" Nano Letters (2019); 19(5):2993-3001.

Lv, P. et al. "Genetically engineered cell membrane nanovesicles for oncolytic adenovirus delivery: A versatile platform for cancer virotherapy—Supporting Information" Nano Letters (2019); 13 pages.

Templeton et al. "Improved DNA: liposome complexes for increased systemic delivery and gene expression" Nature biotechnology (1997); 15(7):647-652.

Xia Q. et al. "Red blood cell membrane-camouflaged nanoparticles: a novel drug delivery system for antitumor application" Acta Pharmaceutica Sinica B (2019); 9(4):675-689.

* cited by examiner

Average Particle Size of Coated and Uncoated Viruses

FIG. 3A-B
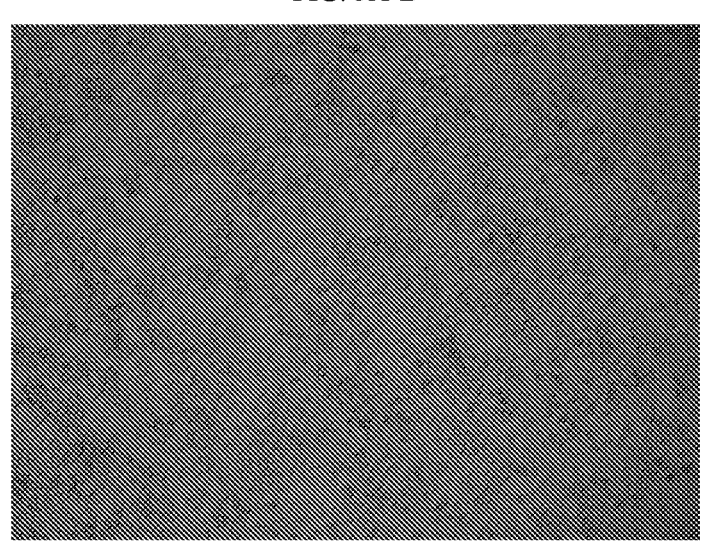
3A
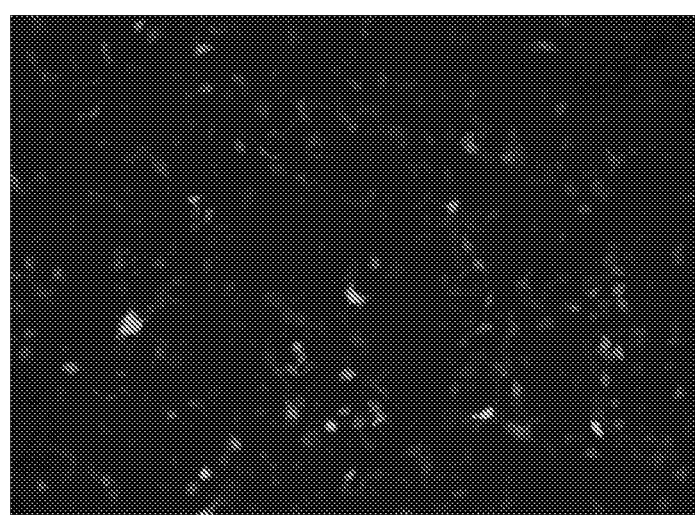
3B

PROCESS OF MAKING MEMBRANE LIPID COATED NANOPARTICLES

BACKGROUND OF THE INVENTION

Oncolytic viruses (OVs) are viruses that preferentially infect and kill cancer cells. The viruses grow and cause lysis (oncolysis) of cancer cells or trigger other mechanisms to disturb the cancer-immunosuppressive microenvironment and trigger the body's immune response to clear cancer cells. Recent successful clinical data and drug approvals have increased public attention on oncolytic virotherapy. The use of oncolytic virotherapy can be combined with other drugs, immune check point inhibitors, and T-cell therapy to improve outcomes for cancer patients.

Routes of delivery of OVs include intratumoral (i.t.) injection, intravenous (i.v.) delivery, and intra-peritoneal delivery, where intratumoral injection is applied mostly.

SUMMARY OF THE INVENTION

In accordance with the present invention, the present invention provides a process of making a particular nanoparticle comprising combining an inner core comprising a virus, or the like, and an outer surface comprising a cellular derived from a cell in solution; applying a process of extrusion to said solution to form a nanoparticle comprising said inner core coated with said outer surface.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3AB illustrate the images of fluorescent microscopy study results of RBC membrane coated virus nanoparticles. FIG. 3A provides a brightfield picture of A529 cancer cells plated in a tissue culture well. FIG. 3B provides a fluorescent picture of the same field of view after treated with the nanoparticles.

DETAILED DESCRIPTION OF THE INVENTION

Figures 1, 2:
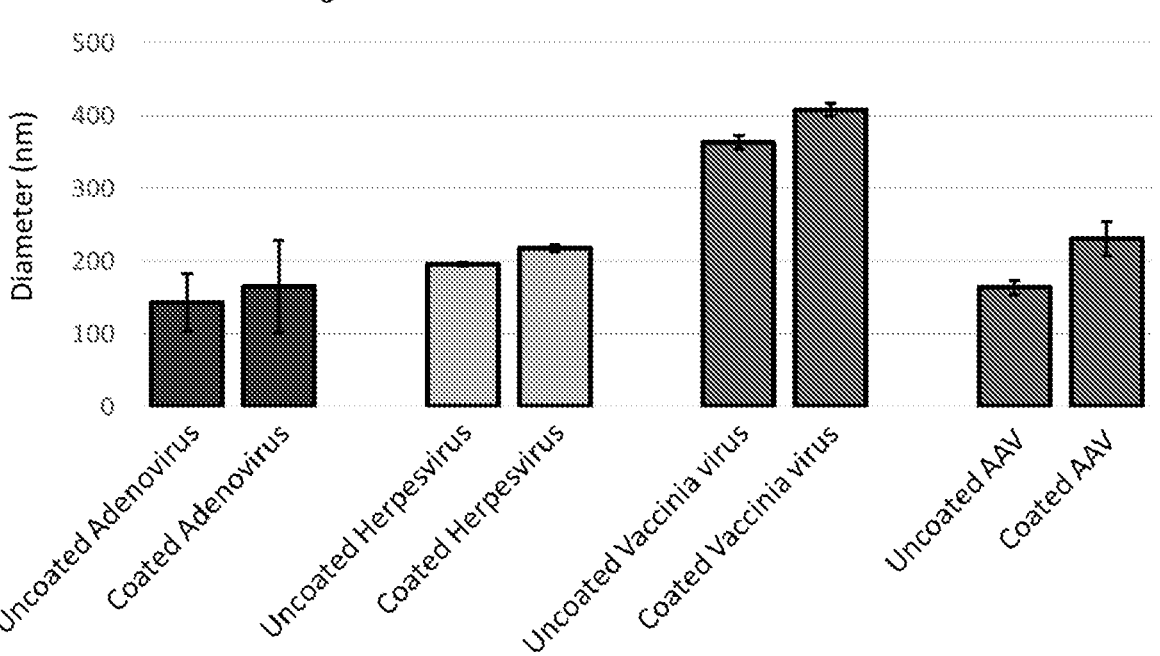
FIG. 1. Shows a chart of average particle diameters of the bare adenovirus in comparison with the coated adenovirus by an exemplary extrusion processing described herewith.
FIG. 2 shows a chart of average particle diameters of various bare viruses in comparison with the coated viruses by an exemplary extrusion processing described herewith.

Currently, most oncolytic virus therapies are limited to local regional injection (such as intratumoral, i.t.), and whether a single injection is enough to achieve therapeutic effect is still under investigation. It is known that some OVs have been shown to have an acute, transient toxicity profile, and thus injecting the virus may induce a competitive immune response against the virus rather than against the tumor cells. Also, there is a problem for intravenous delivery of OVs where OVs may be cleared rapidly from the bloodstream, thus requiring frequent or high-dose administrations, leading to increased therapy costs and potential safety issues. As such, it is needed to provide a composition comprising OVs that can be administered and remained in circulation for extended periods of time for ultimate delivery of therapeutic agents to targeted cells.

It is known in the art that to achieve stealth moiety on nanoparticle, the adoption of polyethylene glycol (PEG) is employed. However, an anti-PEG immunological response may be triggered and thus such approach is problematic. Alternative approaches such as utilizing zwitterionic materials (e.g., poly(carboxybetaine) and poly(sulfobetaine)) have been proposed.

Recently, a top-down biomimetic approach to provide functionalized nanoparticles by coating with natural erythrocyte membranes, including both membrane lipids and associated membrane proteins was realized, providing long-circulating cargo delivery. See C-M. J. Hu et al., "Erythrocyte membrane-camouflaged polymeric nanoparticles as a biomimetic delivery platform," Proc. Natl. Acad. Sci. USA 2011, July 5; 108(27): 10980-10985. Particularly, the membrane lipids derived from a blood cell (e.g., red blood cell (RBC), white blood cell (WBC), or platelet) are of particular interests to coat various of materials but not the oncolytic viruses, or the like.

Various attempts to prepare RBC coated nanoparticles with oncolytic virus core were tried but not successful following the known methods except the use of a particular method via sonication. While not wishing to be bound by any theories, the fact that viruses are easy to be deactivated due to certain physical and chemical conditions does limit how a skilled person in the art to process the virus. For example, it is known that certain viruses can be deactivated by pressure, heat, and/or chemicals such as high concentrated alcohol solutions.

Extrusion is a process used to create objects of a fixed cross-sectional profile. A material is pushed through a die of the desired cross-section. The two main advantages of this process over other manufacturing processes are its ability to create very complex cross-sections, and to work materials that are brittle, because the material only encounters compressive and shear stresses. It also forms parts with an excellent surface finish. Industrial level extrusion application involves pressure, temperature, heating and cooling controls.

Just like the difficulty handling of a live virus, the process of utilizing a cell membrane, such as red blood cell membrane is not easy as well. There are provided methods of making RBC membrane vesicles via sonication and extrusion. See e.g., Luk, et al., Nanoscale, 2014, 6, 2730-2737. In Luk, PLGA polymer core was coated with RBC membrane through a solvent displacement method followed by extrusion through a 100 nm polycarbonate porous membrane using an Avanti mini extruder. It is reported that extruded vesicles are only produced above a certain threshold extrusion pressure and have sizes that depend on the extrusion pressure. The minimum pressure appears to be associated with the lysis tension of the lipid bilayer rather than any bending modulus of the system. The flow rate of equal concentration lipid solutions through the pores, after being corrected for the viscosity of water, is independent of lipid properties. See Hunter, et al., Biophysical Journal, 74, 1998, 2996-3002.

However, despite the use of extrusion to prepare RBC membranes, there is no extrusion process of making nanoparticles comprising virus core with RBC membrane found. It is likely the process is not suitable for encapsulation of viruses by RBC membrane due to the pressure, heat, and/or other factors involved in the process.

Indeed, it is known in the art that the process of pressure-based virus inactivation is a promising alternative and an industrially mature technology. See, e.g., Dumard et al., PLOS ONE, November 2013, volume 8, issue 11, e80785. For example, it is known that adenoviruses are resistant to UV treatment, but low-pressure UV inactivates adenoviruses. Thus, one of ordinary skilled in the art would not consider using the process of extrusion on viruses as the process may inactivate viruses.

In accordance with the practice of the invention, it is surprisingly found that a condition involving extrusion may be used to prepare invention nanoparticles comprising virus core described herein without inactivating the viruses making such process a viable method to prepare said nanoparticles.

In some embodiments, the invention process involves a preparation of a pre-coated solution comprising virus particles, and cell-derived membrane in a suitable solvent (e.g., a water-based solvent) prior to the step of extrusion. Examples of virus particles are, but is not limited to, adeno-associated viruses, adenoviruses, herpes simplex viruses, and vaccinia viruses. The concentration of the virus, measured in number of genome copies, in some embodiments, ranges from $10^4$ genome copies per mL to $10^{15}$ genome copies per mL. The concentration of blood-derived membrane is measured in overall protein concentration, and in some embodiments, ranges between 0.001 mg per mL to 10 mg per mL.

Depending on the size of the virus used in the process of making, a nanopore membrane with pores approximately equals to or larger than the size of the virus may be used. For example, a virus of known size of about 100 nm may be matched with a nanopore membrane of pore size 100 nm or higher.

Any suitable devices that are used for the method/process of extrusion are readily recognized by a skilled person in the art. For example, a device containing an injection port into a chamber that holds the nanopore fixed in place without allowing for leaking, and with an extrusion port across the nanopore is used in accordance with the practice of the invention.

Then, the pre-coated solution described above is loaded into the chamber containing the nanopore membrane via the injection port, and surprisingly, with the application of some pressure (e.g., about 5-10 psi), the solution forces through the nanopore membrane, emerges on the other size and is collected on the extrusion port. Physical forces exerted during this process causes disruption in the cell-derived membrane. The disrupted membrane then envelopes and reforms around the virus particles, thereby coating or encapsulating some of the viral particles. There were several attempts utilizing the extrusion methods known in the art as discussed. However, it was found surprisingly that only a low-pressure extrusion process in accordance with the practice of the invention provides satisfactory virus encapsulation nanoparticles. This extrusion process may be repeated, typically between 15-30 times, to ensure a thorough encapsulation of almost all of the virus particles in solution. In some embodiments, the extrusion process is repeated 10-30 times, 15-30 times, 15-25 times, or 15-20 times. The physical act of adding a coating onto the virus increases the size of the resulting particle. Thus, the proof of encapsulation is evidenced by an increase in particle size diameter.

The term "oncolytic virus" referred herein includes non-limited examples of herpesvirus; vaccinia virus; reovirus; adenovirus; measles virus, parvovirus, or combinations thereof.

It is known in the art that viruses can be used as vectors for delivery of suicide genes, encoding enzymes that can metabolize a separately administered non-toxic pro-drug into a potent cytotoxin, which can diffuse to and kill neighboring cells. Thus, the therapeutic agent disclosed here also includes such vectors, suicide genes, or encoding enzymes.

In accordance with the present invention, it is found surprising a process to make a nanoparticle comprising combining an inner core comprising a virus (a therapeutic agent), or the like, and an outer surface comprising a cellular membrane derived from a cell in a solution; applying extrusion to said solution to form a nanoparticle comprising said inner core coated with said outer surface. In some embodiments provide a nanoparticle comprising an inner core comprising a virus; and an outer surface comprising a cellular membrane derived from a cell. In certain embodiments, said virus is an oncolytic virus. In certain embodiments, said oncolytic virus is herpesvirus; vaccinia virus; reovirus; adenovirus; measles virus, parvovirus, or combinations thereof. In certain embodiments, said virus is adenovirus.

In some embodiments, said cell is a blood cell, an adipocyte, a stem cell, an endothelial cell, an exosome, a secretory vesicle or a synaptic vesicle. In certain embodiments, said blood cell is red blood cell, white blood cell, or platelet. In certain embodiments, said blood cell is red blood cell.

In some embodiments provide a process of making a nanoparticle comprising combining an inner core comprising a virus, and an outer surface comprising a cellular membrane derived from a cell in a solution; applying extrusion to said solution to form a nanoparticle comprising said inner core coated with said outer surface. In certain embodiments, said solution is a salt-water solution, or a non-salt water solution comprises sugar, or the like (such as a component with similar property of a sugar in water solution). In certain embodiments, said non-salt water solution is a sugar solution. In certain embodiments, said sugar solution is sucrose, or dextrose containing solution. In some embodiments, said virus is an oncolytic virus. In certain embodiments, said oncolytic virus is herpesvirus; vaccinia virus; reovirus; adenovirus; measles virus, parvovirus, or combinations thereof. In certain embodiments, said oncolytic virus is adenovirus. In some embodiments, said cell is a blood cell, an adipocyte, a stem cell, an endothelial cell, an exosome, a secretory vesicle or a synaptic vesicle. In certain embodiments, said blood cell is red blood cell, white blood cell, or platelet. In certain embodiments, said blood cell is red blood cell.

The invention provides a cellular membrane derived nanoparticle for delivering of a therapeutic agent, such as an oncolytic virus. The agent is essentially camouflaged by coating the therapeutic agent such as oncolytic virus with cellular membrane lipids.

In some embodiments, a therapeutic agent such as oncolytic virus is coated with lipids compatible with circulation within the bloodstream of a subject (e.g., a patient). This allows delivery of the agent to tumor vasculature via the EPR (enhanced permeability and retention) effect, where certain molecules tend to accumulate in tumor tissues more than in normal tissues. The EPR effect is usually employed to describe nanoparticle and liposome delivery to cancer tissue. One of many examples is the work regarding thermal ablation with gold nanoparticles. Thus, in some embodiments, the nanoparticles disclosed herein would accumulate near a tumor's vasculature, and the therapeutic agents (e.g., a OV) will come into contact with cancer cells. The OV then infects the cell, resulting in cell lysis, death, or removal.

In some embodiments provide the method to prepare the nanoparticles disclosed herein. For example, blood cells can be purified from whole blood or from processed red blood cells obtained from a blood supplier. RBCs are particularly useful as a membrane source because of their abundance in human blood and the ease of collecting blood from individual donors. RBCs can be provided in the form of erythrocyte ghosts (or RBC ghosts), where the internal proteins have been depleted, leaving the membrane components essentially intact. The use of RBC ghosts also reduces the presence of RBC cellular proteins that may interfere during the coating process. In some embodiments, the RBC is a type 0-negative blood cell (i.e., an "universal donor"). Such membrane source can be used in the preparation of the nanoparticles to deliver the therapeutic agent (e.g., an OV) to a greater number of subjects. In certain embodiments, one can use cell membranes derived from the same patient for personalized batches of nanoparticles.

Compared to other platforms, for example a PEG coating nanoparticle, the RBC membrane derived nanoparticle has many surface markers such as CD47, CD59 (MAC-inhibitory protein, avoiding complement cell lysis), CD55 (DAF), CD35 (CR1) and other members in immunoglobulin superfamily to protect itself from body clearance. In some embodiments, the cell membrane used for coating herein can further incorporate non-lipid components, such as cell surface markers, MHC molecules, and glycoproteins. In other embodiments, the cell membrane can further incorporate hydrophilic components, such as PEG.

The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom.

As used herein, the term "naturally occurring" refers to one existing in nature.

As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell and the prepared or isolated membrane can be combined with other substances or materials to form a derived membrane. In another example, a cell can be recombinantly engineered to produce "non-natural" or "natural" substances that are incorporated into its membrane in vivo, and the cellular or viral membrane can be prepared or isolated from the cell to form a derived membrane.

A cellular membrane can be prepared by known methods. For example, cells can be broken using a microfluidizer (MF), or a hypotonic solution, such as water, followed by ultrafiltration or diafiltration with saline or PBS. In some cases, a solution with higher ionic strength has been useful for removing blood from pork liver, so a PBS or NaCl solution can help remove intracellular mass through the filtration process. An anticoagulant, such as EDTA, can also be used, for example during diafiltration to remove impurities. In some embodiments, a Tangential Flow Filtration (TFF) device or centrifugation can be used to purify the membranes. The purified membrane components can be tested for the presence of cellular proteins, such as by a BCA protein test. Preferably, most non-membrane components are removed prior to coating.

Despite the much efforts, it was found that following the known methods, such as the procedures in US2013/0337066, a virus such as an oncolytic virus or a CRISPR, a DNA sequence from viruses, cannot be coated or encapsulated by a cell membrane (e.g., a RBC membrane). It is surprisingly found that the cell membranes (e.g., RBC ghosts) coat the virus, or the like, only in certain conditions. The process to prepare the nanoparticles disclosed herein requires extrusion of the mixture of RBC ghosts and OVs in a solution. In certain embodiments the pressure applied in invention extrusion process is about 1 to 300 psi depending on the pore size of porous membrane is used. In certain embodiments, the pressure applied in the process is about 5 to 300, 5 to 200, 5 to 100, 5 to 50, 5 to 40, 5 to 30, 5 to 20, or 5 to 10 psi. In certain embodiments, the pressure applied in the process is about 5 to 10 Psi.

In accordance with the practice of the invention, viruses suitable for coating include oncolytic viruses as well as other viruses that can infect a cancer cell. Viruses can have enveloped or noneveloped forms. In some embodiments, viral vectors are preferred because they can infect a cancer cell and replicate (replication competency).

In some embodiments provide a process of making a nanoparticle comprising combining an inner core comprising a virus, and an outer surface comprising a cellular membrane derived from a cell in a water solution; applying a process of extrusion to said solution of mixture to form a nanoparticle comprising said inner core coated with said outer surface. In some embodiments, a pressure of 5-300 psi is applied in said applying extrusion process. In certain embodiments, said extrusion step requires pressure of 5-100 psi. In some embodiments, said extrusion step is repeated at least 10 times, or 10 to 30 times, or 10 to 20 times. In some embodiments, said water solution is a salt water solution or a non-salt water solution. In certain embodiments, said water solution is a non-salt water solution comprising sugar, or a component with similar property of a sugar in water solution. In certain embodiments, said non-salt water solution is a sugar solution such as sucrose, or dextrose containing solution. In some embodiments, said virus is an oncolytic virus such as herpesvirus; vaccinia virus; reovirus; adenovirus; measles virus, parvovirus, or combinations thereof. In some embodiments, said virus is adenovirus. In some embodiments, said cell is a blood cell, an adipocyte, a stem cell, an endothelial cell, an exosome, a secretory vesicle or a synaptic vesicle. In some embodiments, said blood cell is red blood cell, white blood cell, or platelet. In certain embodiments, said blood cell is red blood cell.

Certain Pharmaceutical and Medical Terminology

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The term "pharmaceutical composition" refers to a mixture of a nanoparticle (i.e., nanoparticle described herein) with other chemical components, such as, disintegrators, binders, lubricants, carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

All of the various embodiments or options described herein can be combined in any and all variations. The following Examples serve only to illustrate the invention and are not to be construed in any way to limit the invention.

EXAMPLES

Example 1. Exemplary Preparation of
Nanoparticles Coated by Cell Membrane via
Extrusion The cell membrane preparation (e.g., a RBC ghost preparation) is known the art. Here a non-limited example of preparing a cell membrane, a RBC cell membrane, was followed to provide an exemplary cell membrane for invention nanoparticles preparation.

Materials:

Virus (with known particle diameter, e.g., 10^12 to 10^13 PFU for adenovirus, 10^8 to 10^9 PFU for herpes virus, 10^8 to 10^9 PFU for vaccinia virus, 10^11 to 10^13 virus particles/mL for adeno-associated virus).

Blood-derived membrane

Nanopore membrane filters (e.g., Polycarbonate filters, Pore size 800 nm, 400 nm, and 200 nm)

Extrusion device 2 gas-tight syringes

DI water

Procedure: To encapsulate a virus with blood-derived membrane, a solution containing high concentrations of membrane (e.g., RBC cell membrane) and viruses was extruded through a nanopore membrane repeatedly (about 20 times). The first extrusion with a nanopore membrane of larger pore size was performed (1600 nm or 800 nm), and then the resulting eluent was collected. The eluent was then subject to more extrusions with smaller pore sizes (e.g., 800→400→200), and finishing with a pore size slightly larger than the size of the virus. For example, if the virus is 120-150 nm in diameter, a nanopore membrane of pore size 200 nm is used.

An exemplary method for extrusion is detailed below.

Pre-extrusion Preparation

Assembled the extrusion device with the nanopore membrane filters sandwiched.

Loaded 100 uL of sterile DI water into the gastight syringe

Passed 100 uL of sterile DI water using the gastight syringe through the membrane to pre-wet the membrane.

Extrusion through a Nanopore Membrane

1. To 500 uL-1000 uL of membrane (e.g., a RBC membrane), added enough about 1-2% of virus (e.g., adenovirus) by volume (5-10 ul in 500 uL) and mixed homogenously.
2. Loaded the virus/membrane solution ("V/M solution") into the gastight syringe
3. Inserted gastight syringe into the extrusion setup.
4. Inserted empty gastight syringe across from the loaded syringe in the extrusion setup.
5. Pushed the V/M solution by low pressure around 5 to 10 psi across the membrane from the load syringe to the empty syringe.
6. Pushed the V/M solution back to the now empty (previously loaded syringe)
7. Repeated steps 5-6 at least 10× to ensure that the V/M solution passes through the nanopore membrane, and in some instance, no less than 20×.

The resulted coated nanoparticles were imaged by Transmission Electron Microscopy (TEM) and the particle diameters were measured. FIG. 1 shows a chart of average particle diameters of the bare adenovirus in comparison with the coated adenovirus by an exemplary extrusion processing described herewith. The larger diameter of the coated virus clearly demonstrates the successful process of making the coated virus via the invention method.

The invention process is particularly useful in the preparation of various coated viruses. FIG. 2 shows a chart of average particle diameters of various bare viruses in comparison with the coated viruses by an exemplary extrusion processing described herewith.

Example 2. Fluorescent Microscopy Study Results
of RBC Membrane Coated Virus Nanoparticles Fluorescent microscopy was used to demonstrate the ability of the virus to remain infectious after the extrusion process. A529 cancer cells were plated into a well on a 24-well tissue culture plate and allowed to grow. As they are growing, we treated them with EDM-coated adenovirus for 10 minutes, before media containing the virus is removed, the cells are rinsed with PBS before replacement in regular growth media. The EDM-coated adenovirus used contained a gene that would express fluorescent protein when the virus infects the cell.

FIG. 3A provides a brightfield picture of A529 cancer cells plated in a tissue culture well. FIG. 3B provides a fluorescent picture of the same field of view, showing the cancer cells expressing the fluorescent protein after successful infection by the coated adenovirus. Thus, it is surprisingly and clearly demonstrated that the invention extrusion process did not inactivate the virus coated by RBC membranes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process of making a nanoparticle comprising an inner core comprising a virus, and an outer surface comprising a cellular membrane derived from a cell, said process comprising the steps of:

providing a mixture of a virus and a cellular membrane derived from a cell in a water solution; and applying a process of extrusion to said mixture to form the nanoparticle.

2. The process of claim 1, wherein a pressure of 5-300 psi is applied in said applying extrusion process.

3. The process of claim 2, wherein said extrusion step requires pressure of 5-100 psi.

4. The process of claim 1, wherein said extrusion step is repeated at least 10 times.

5. The process of claim 1, wherein said water solution is a salt water solution.

6. The process of claim 1, wherein said water solution is a non-salt water solution comprising sugar, or a component with similar property of a sugar in water solution.

7. The process of claim 6, where said non-salt water solution is a sugar solution.

8. The process of claim 7, wherein said sugar solution is sucrose, or dextrose containing solution.

9. The process of claim 1, wherein said virus is an oncolytic virus.

10. The process of claim 9, wherein said oncolytic virus is herpesvirus;

vaccinia virus; reovirus; adenovirus; measles virus, parvovirus, or combinations thereof.

11. The process of claim 10, wherein said virus is adenovirus.

12. The process of claim 1, wherein said cell is a blood cell, an adipocyte, a stem cell, an endothelial cell, an exosome, a secretory vesicle or a synaptic vesicle.

13. The process of claim 12, wherein said blood cell is red blood cell, white blood cell, or platelet.

14. The process of claim 13, wherein said blood cell is red blood cell.

* * * * *